US008309304B2

(12) United States Patent
Yam et al.

(10) Patent No.: US 8,309,304 B2
(45) Date of Patent: *Nov. 13, 2012

(54) LABEL-FREE OPTICAL SENSING AND CHARACTERIZATION OF BIOMOLECULES BY $D^8$ OR $D^{10}$ METAL COMPLEXES

(75) Inventors: Vivian Wing-Wah Yam, Hong Kong (HK); Cong Yu, Hong Kong (HK); Kenneth Hoi-Yiu Chan, Kowloon (HK); Keith Man-Chung Wong, Howloon (HK)

(73) Assignee: The University of Hong Kong, Hong Kong (CN)

( * ) Notice: Subject to any disclaimer, the term of this patent is extended or adjusted under 35 U.S.C. 154(b) by 1259 days.

This patent is subject to a terminal disclaimer.

(21) Appl. No.: 12/017,108

(22) Filed: Jan. 21, 2008

(65) Prior Publication Data

US 2008/0153103 A1 Jun. 26, 2008

Related U.S. Application Data

(63) Continuation-in-part of application No. 11/625,109, filed on Jan. 19, 2007.

(60) Provisional application No. 60/772,090, filed on Feb. 10, 2006.

(51) Int. Cl.
*C12Q 1/68* (2006.01)
*G01N 33/566* (2006.01)

(52) U.S. Cl. ........................................ 435/6.1; 436/501

(58) Field of Classification Search ........................ None
See application file for complete search history.

(56) References Cited

U.S. PATENT DOCUMENTS

| 5,985,567 | A | 11/1999 | Rampal |
| 6,132,972 | A | 10/2000 | Shigemori et al. |
| 2001/0046670 | A1 | 11/2001 | Brookes |
| 2004/0033518 | A1 | 2/2004 | Wittwer |
| 2004/0219556 | A1 | 11/2004 | Bazan |
| 2005/0048485 | A1 | 3/2005 | Kurane |
| 2005/0059042 | A1 | 3/2005 | Rothberg |

FOREIGN PATENT DOCUMENTS

| CN | 2489922 | 6/2003 |
| GB | 2318791 | 5/1998 |
| JP | 61219400 | 9/1986 |
| JP | 11151100 | 6/1999 |
| WO | 9846790 | 10/1998 |
| WO | WO 99/42616 | 8/1999 |
| WO | 03091408 | 11/2003 |
| WO | 20041111602 | 12/2004 |

OTHER PUBLICATIONS

Ratilla (PhD Thesis Iowa State University, Ames Laboratory, U.S. DOE, Oct. 9, 1990).*
Chan et al. (Chem. Bio. Chem. 2003, 4, 62-68).*
Ma et al. (Chem. Eur. J. 2003, 9, 6133-6144).*
Keller, H.J., "Linear Chain Platinum Haloamines," Extended Linear Chain Compounds /edited by Joel S. Miller (1982), pp. 357-401.
Martin, D.S. Jr. "Optical Properties of Linear Chain Haloamine Platinum Complexes" Extended Linear Chain Compounds /edited by Joel S. Miller (1982), pp. 409-449.
KOKAI Open Application No. JP2005000088, published Jan. 6, 2005 (Shigemori).
Adamovich et al., "High Efficiency Single Dopant White Electrophosphorescent Light Emitting Diodes," New Journal of Chemistry, 2002, 26, 1171-1178.
Blackburn et al. ed., "Nucleic Acids in Chemistry and Biology", Oxford University Press, Oxford, 1996, pp. 331-337.
Bailey et. al., "Electronic Spectroscopy of Chloro(terpyridine)platinum(II)" Inorganic Chemistry, 1995, 34, 4591-4599.
Bloomfield et al., "Nucleic Acids: Structures, Properties, and Functions," University Science Books, California, 2000, pp. 311-312; 507-517.
Creighton, "Proteins: Structure and Molecular Properties", W. H. Freeman and Company, New York, 1993, pp. 355-363.
Fasman ed., "Circular Dichroism and the Conformational Analysis of Biomolecules," Plenum Press, New York, 1996, pp. 202-251.
Gaylord et al., "DNA Detection Using Water-Soluble Conjugated Polymers and Peptide Nucleic Acid Probes," 2002, 99, PNAS 10954-10957.
Goshe et al., "Supramolecular Recognition. Terpyridyl Palladium and Platinum Molecular Clefts and Their Association with Planar Platinum Complexes," Journal of the American Chemical Society, 2003, 125, 444-451.
Han et al., "Interactions of TMPyP4 and TMPyP2 with Quadruplex DNA. Structural Basis for the Differential Effects on Telomerase Inhibition," Journal of the American Chemical Society, 1999, 121, 3561-3570.
Herber et al., "Origin of Polychromism of Cis Square-Planar Platinum(II) Complexes: Comparison of Two Forms of [Pt(2,2'-bpy)(CI)$_2$]," Inorganic Chemistry, 1994, 33, 2422-2426.
Houlding et. al., "The Effect of Linear Chain Structure on the Electronic Structure of Platinum(II) Diimine Complexes," Coordination Chemistry Reviews, 1991, 111, 145-152.
Hill et. al., "Spectroelectrochemistry and Dimerization Equilibria of Chloro(terpyridine)platinum(II). Nature of the Reduced Complexes," Inorganic Chemistry, 1996, 35, 4585-4590.

(Continued)

*Primary Examiner* — Michael G Hartley
*Assistant Examiner* — Melissa Perreira
(74) *Attorney, Agent, or Firm* — Robert D. Katz; Eaton & Van Winkle LLP

(57) ABSTRACT

The present invention provides a composition for detecting and/or characterizing a multiple-charged biomolecule comprising a charged d8 or d10 metal complex, wherein the metal complex electrostatically binds to the multiple-charged biomolecule to induce aggregation and self-assembly of the metal complex through metal-metal interactions, π . . . π interactions, or a combination of both interactions. The present invention further provides assay methods and kits for label-free optical detection and/or characterization of biomolecules carrying multiple charges, e.g., single-stranded nucleic acids, using a composition comprising a charged $d^8$ or $d^{10}$ metal complex.

48 Claims, 12 Drawing Sheets

OTHER PUBLICATIONS

Towbin et. al., "Clinical Implications of Basic Research; New Revelations about the Long-QT Syndrome," New England Journal of Medicine, 1995, 333, 384-385.

Jennette et. al., "Metallointercalation Reagents. 2-Hydroxyethanethiolato (2,2',2'''-terpyridine)platinum(II) Monocation Binds Strongly to DNA by Intercalation," PNAS, 1974, 71, 3839-3843.

Mitcheson et. al., "A Structural Basis for Drug-Induced Long QT Syndrome," PNAS, 2000, 97, 12329-12333.

Kakar et. al., "Reconstitution of the Mitochondrial Non-Selective Sodium/Hydrogen Ion (Potassium/Hydrogen Ion) Antiporter into Proteoliposomes," Journal of Biological Chemistry, 1989, 264, 5846-5851.

Kang et. al., "Crystal Structure of Four-Stranded Oxytricha Telomeric DNA," Nature, 1992, 356, 126-131.

Keating et. al., "Molecular and Cellular Mechanisms of Cardiac Arrhythmias," Cell, 2001, 104, 569-580.

Laughlan et. al., "The High-Resolution Crystal Structure of a Parallel-Stranded Guanine Tetraplex," Science, 1994, 265, 520-524.

Li et al., "Label-Free Colorimetric Detection of Specific Sequence in Genomic DNA by the Polymerase Chain Reaction," Journal of the American Chemical Society, 2004, 126, 10958-10961.

Lippard, "Platinum Complexes: Probes of Polynucleotide Structure and Antitumor Drugs," Accounts of Chemical Research, 1978, 11, 211-217.

Miller JS, (ed.), (1982) *Extended Linear Chain Compounds*, vol. 1 (Plenum Press, New York).

Nagatoishi et. al., "A Pyrene-Labeled G-Quadruplex Oligonucleotide as a Fluorescent Probe for Potassium Ion Detection in Biological Applications," Angewandte Chemie International Edition, 2005, 44, 5067-5070.

Nagatoishi et. al., "G Quadruplex-Based FRET Probes with the Thrombin-Binding Aptamer (TBA) Sequence Designed for the Efficient Fluorometric Detection of the Potassium Ion," ChemBioChem, 2006, 7, 1730-1737.

Recanatini et. al., "QT Prolongation Through hERG $K^+$ Channel Blockade: Current Knowledge and Strategies for the Early Prediction During Drug Development," Medicinal Research Reviews, 2005, 25, 133-166.

Sanguinetti et. al., "hERG Potassium Channels and Cardiac Arrhythmia," Nature, 2006, 440, 463-469.

Sen et al., "A Sodium-Potassium Switch in the Formation of Four-Stranded G4-DNA," Nature, 1990, 344, 410-414.

Williamson et. al., "Monovalent Cation-Induced Structure of Telomeric DNA: The G-Quartet Model," Cell, 1989, 59, 871-880.

Yam et al., "Synthesis, Luminescense, Electrochemistry, and Ion-Binding Studies of Platinum(II) Terpyridyl Acetylide Complexes," Organometallics, 2001, 20, 4476-4482.

Yam et al., "Solvent-Induced Aggregation through Metal•••Metal/π•••π Interactions: Large Solvatochromism of Luminescent Organoplatinum(II) Terpyridyl Complexes," Journal of the American Chemical Society, 2002, 124, 6506-6507.

Yam et al., "Luminescent Platinum(II) Terpyridyl Complexes: Effect of Counter Ions on Solvent-Induced Aggregation and Color Changes," Chem.J. Eur., 2005, 11, 4535-4543.

Yip et. al., "Luminescent Platinum(II) Complexes. Electronic Spectroscopy of Platinum(II) Complexes of 2,2':6',2'''—Terpyridine (terpy) and *p*-Substituted Phenylterpyridines and Crystal Structure of [Pt(terpy)Cl][$CF_3SO_3$]," Journal of the Chemical Society, Dalton Transtractions, 1993, 2933-2938.

Yu et al., "Polymer-Induced Self-Assembly of Alkynylplatinum(II) Terpyridyl Complexes by Metal•••Metal/π•••π Interactions," Angewandte Chemie International Edition, 2005, 44, 791-794.

Yu et al., "Single-Stranded Nucleic Acid-Induced Helical Self-Assembly of Alkynylplatinum(II) Terpyridyl Complexes," Proceedings of PNAS, 2006, 103, 19652-19657.

Yu et al., "Polyelectrolyte-Induced Self-Assembly of Positively Charged Alkynylplatinum(II) Terpyridyl Complexes in Aqueous Media," Manuscript pp. 1-34, Chemistry 2008, 14, 4577-84.

Ueyama, H.; Takagi, M.; Takenaka, S. "A Novel Potassium Sensing in Aqueous Media with a Synthetic Oligonucleotide Derivative. Fluorescence Resonance Energy Transfer Associated with Guanine Quartet-Potassium Ion Complex Formation," J. Am. Chem. Soc. 2002, 124, 14286.

\* cited by examiner

# US 8,309,304 B2

LABEL-FREE OPTICAL SENSING AND CHARACTERIZATION OF BIOMOLECULES BY $D^8$ OR $D^{10}$ METAL COMPLEXES

CROSS REFERENCE TO RELATED APPLICATION

This application is a continuation-in-part of U.S. patent application Ser. No. 11/625,109, filed on Jan. 19, 2007, which claims priority of U.S. Provisional Patent Application Ser. No. 60/772,090, filed Feb. 10, 2006. The foregoing applications are incorporated herein by reference.

FIELD OF THE INVENTION

The present invention relates to procedures and materials for label-free optical detection and characterization of biomolecules carrying multiple charges in a sample.

BACKGROUND OF THE INVENTION

Nucleic acids, either DNA or RNA, single-stranded or double-stranded, are the most fundamental and important class of biomolecules in a living cell. DNA encodes the genetic information that passes from generation to generation. Through transcription, the coded information is transferred to mRNA, which binds to ribosome (specific ribosomal RNA and protein complex). With the assistance of tRNA, which contains an anticodon and a specific amino acid, the carried information of mRNA is translated into a precise sequence of a polypeptide of 20 amino acids. Folding of the polypeptide into a well-defined three-dimensional structure gives rise to a protein. Many classes of proteins act as building blocks, enzymes, and regulation factors. Together with other classes of biomolecules, proteins are responsible for the structure and proper function of a living cell.

Since nucleic acids carry multiple negatively charged phosphate functional groups, they are polyanions. Under physiological conditions, poly(aspartic acid) and poly(glutamic acid) form polycarboxylates, which are also polyanions. On the other hand, polylysine, polyarginine, and polyhistidine (in an acidic aqueous solution) carry multiple positive charges, and are considered polycations. Many proteins, when the solution pH is not at their isoelectric point (pI) value, carry net positive or negative multiple charges (21). In light of the above, methods that can detect and characterize biomolecules with multiple charges are of great importance, which can not only help us to understand how the cell functions, assist biological/biochemical research, but may also provide ways to facilitate biomedical research, clinical diagnosis, and new drug development.

The intriguing structural and bonding properties of square-planar $d^8$ or $d^{10}$ metal complexes have attracted long-standing interest, and more so recently with the growing interest in the spectroscopic properties associated with this class of metal complexes. These metal complexes are known to display a strong tendency towards the formation of highly-ordered extended linear chains or oligomeric structures in the solid state. The extent of the metal-metal interaction and the $\pi$ . . . $\pi$ stacking of the aromatic ligand have led to the observation of interesting spectroscopic and luminescence properties, and recent reports based on the utilization of these observations for molecular recognition, chemosensing, and optoelectronic applications have been made (17, 19, 24, 26-28, 30, 37, 38, 45-48).

A representative example of the class of the aforementioned $d^8$ or $d^{10}$ metal complexes is the alkynylplatinum(II) terpyridyl complexes (45-47). By changing the solvent polarity, or using a polyelectrolyte, namely polyacrylate (a polyanion), the $d^8$ or $d^{10}$ metal complexes are induced to aggregate and self-assemble, thereby creating observable dramatic changes in the UV/vis and emission spectra (46, 49). In addition, when the complex was mixed with single-stranded nucleic acid in an aqueous solution, dramatic UV/vis and emission spectral changes were also observed; the spectral changes were closely related to the structure of the single-stranded nucleic acid as well as the structural properties of the complex (50).

There are a number of assay methods available nowadays for the detection and characterization of multiple-charged biomolecules. However, most of the commonly used existing methods require sophisticated analytical techniques and expensive instrumentation. Many of these methods require labeling with a detectable group, which can be a radioisotope or a fluorescent substance, as well as hybridization procedures for nucleic acid detection. Hence, such methods usually demand high financial cost and are technically complicated and time-consuming.

The importance of our metal complex self-assembly related bio-sensing technology invention can be further illustrated by the following important areas of nucleic acid sensing related research that have been under our extensive investigation.

One important class of nucleic acid is telomeric DNA, which is located at the end of linear eukaryotic chromosomes, and consists of simple tandem repeats of guanine-rich sequences. The majority of telomeric DNA is double-stranded, but the extreme 3' ends are single-stranded, which have the propensity to form four-stranded structures known as G-quadruplexes (18, 20). A guanine quartet is composed of four coplanar guanine nucleobases, stabilized by cyclic Hoogsteen hydrogen bonding, and also by coordination of carbonyl oxygen of guanine with monovalent cations, such as sodium or potassium (FIG. 1). Several quartets stack on top of each other to form G-quadruplex. The enzyme telomerase, a ribonucleoprotein, is a reverse transcriptase. It acts to extend the telomere length, and is inactive in normal human somatic cells, but active in 85-90% of cancer cells. Formation and stabilization of G-quadruplex structure at telomere ends can inhibit telomerase activity, and such strategy has been a very active area of anti-cancer research (25, 33, 35, 43, 44).

In addition, since G-quadruplex formation is stabilized by monovalent cations, it can also be used to selectively sense the presence of potassium ion. Potassium ion ($K^+$) plays an important role in biological systems together with sodium, calcium, magnesium, and other metal ions. Therefore the development of a method to specifically detect potassium ion in a cell is very important.

An important aspect of potassium ion sensing is related to hERG, which is a potassium ion channel. In the late 1990s a number of drugs, approved by the FDA (U.S. Department of Health and Human Services Food and Drug Administration) and available on the market, had to be withdrawn from sales in the US when it was discovered that they were implicated in deaths caused by heart malfunction. It is now known that a side effect of these drugs was the blocking of hERG channels in heart cells. This caused prolongation of action potentials, which are the electrical pulses responsible for controlling heart muscle cells. With the proper control of the rate of heartbeat lost, dangerous arrhythmias could develop, which leads in some cases to death.

An unbalanced $K^+$ concentration is associated with the onset of irregular heartbeat and hERG-blocking properties can end the prospects for a potential drug. However, there is now no simple way to predict how the structure of a drug would determine whether it will block hERG or not. Therefore, testing on these channels needs to be implemented early in the drug-screening procedure. In many companies all drug candidates will be tested for hERG blocking before any further investigation is carried out since there is no point in going on with a compound that can never get into the market. The enormous number of compounds that need to be screened and tested will provide a formidable challenge to pharmaceutical companies. Thus the development of an efficient high throughput assay that is simple, easy to operate and without the need of the talents of highly trained and creative scientists is important. Real-time monitoring of the extracellular concentration of $K^+$ ions (2-10 mM) would require the indicator to exhibit a sufficiently high response in the presence of a complex matrix containing several ions ($Na^+$, $Mg^{2+}$, $Ca^{2+}$, and $Cl^-$) at millimolar concentrations. Thus the challenge will be to develop an assay that can sense selectively $K^+$ ions in the presence of other metal ions, in particular the $Na^+$ and $Ca^{2+}$ ions, as $K^+$ ion plays an important role in biological systems together with $Na^+$, $Mg^{2+}$, $Ca^{2+}$, and other metal ions. At present, the high throughput assay adopted for drug-screening is using Rb as the potassium analogue. Development of a simple real-time assay of stimulated $K^+$ efflux from cells will have the potential to supplement or replace $^{86}Rb$ efflux measurements (29, 31, 32, 34, 41, 42).

Recently, selective and sensitive $K^+$ assays based on G-quadruplex forming oligonucleotides have been reported, as G-quadruplex has a channel at its center with a diameter that correlates well with the ionic radius of $K^+$(1.3 Å). However, these works are mostly based on the dual-labeling of oligonucleotide derivatives with donor and acceptor dyes for fluorescence resonance energy transfer (FRET) and quenching assays (40, 52), involving rather tedious labeling procedures. A related pyrene-labeled oligonucleotide has been developed for selective potassium ion sensing based on excimer emission upon G-quadruplex formation (39), which can be potentially exploited for the real-time monitoring of $K^+$ ions under extracellular conditions. The greater selectivity of these systems towards $K^+$ ions over $Na^+$ ions have made the exploitation of G-quadruplex forming oligonucleotides attractive. However, the involvement of tedious labeling techniques represents a major drawback in these systems. The present assay, which involves a simple label-free method and does not require the tedious labeling or tethering of the platinum(II) indicator via covalent bonding to the G-rich oligonucleotides, is advantageous and is superior to other commonly employed methods, and may be explored for real-time monitoring purposes.

The cleavage of DNA by nuclease such as restriction endonuclease and nonspecific nuclease is involved in many important biological processes, such as DNA replication, recombination, and repair. Single-stranded nucleic acid specific nuclease has been widely used as a tool in molecular biology, such as removal of nonannealed single-stranded nucleic acid tail, hairpin loop, etc. So far, only a few nuclease assay methods are commonly used, such as gel electrophoresis, high performance liquid chromatography (HPLC), sedimentation, and enzyme linked immunosorbent assay (ELISA). These methods are time-consuming, laborious, and usually require substrate labeling.

It has been well-documented that reactive oxygen species such as the superoxide radical anion, hydrogen peroxide, and the hydroxyl radical cause damage to various biomolecules. DNA damage/cleavage by radical species has drawn much attention in recent years, due to its possible involvement in mutagenesis, carcinogenesis, and apoptosis. DNA damage by hydroxyl radicals generates characteristic mutagenic base damages, and the DNA strand breaks into small fragments. Therefore study of the DNA damage/cleavage is of obvious importance. We envisage that our new technique could be used for in vivo detection of reactive oxygen species.

In summary, the present invention provides a novel label-free assay method to sense and characterize multiple-charged biomolecules. Binding of the charged $d^8$ or $d^{10}$ metal complex to the biomolecule carrying opposite charges induces aggregation and self-assembly of the metal complex, and hence gives rise to remarkable UV/vis, emission, and CD intensity changes. The assay not only provides a means to detect the presence of multiple-charged biomolecules, to study their secondary structure and structure/conformation changes, selectively sense specific metal ion, but can also be used to study nucleic acid cleavage by nuclease and damage by reactive oxygen species, and thus can be extended for the detection of nuclease and reactive oxygen species.

SUMMARY OF THE INVENTION

In general, the present invention provides compositions, methods, and kits for detecting and/or characterizing biomolecules carrying multiple charges. A charged $d^8$ or $d^{10}$ metal complex is mixed with a biomolecule. Electrostatic binding of the charged metal complex to the oppositely charged biomolecule induces aggregation and self-assembly of the metal complex via metal-metal interactions and/or $\pi \ldots \pi$ stacking interactions of a corresponding coordinating ligand in the metal complex, which in turn creates remarkable optical property changes, such as UV/vis, emission, and CD intensity changes, of the metal complex (50).

The present invention provides a composition for detecting and/or characterizing a multiple-charged biomolecule comprising a charged $d^8$ or $d^{10}$ metal complex, wherein the metal complex electrostatically binds to the multiple-charged biomolecule to induce aggregation and self-assembly of the metal complex through metal . . . metal interactions, $\pi \ldots \pi$ interactions, or a combination of both interactions.

The present invention also provides an assay method for detecting the presence of a target multiple-charged biomolecule in a sample, which comprises: (a) the combination of a charged $d^8$ or $d^{10}$ metal complex, wherein the metal complex contains at least one transition metal and at least one corresponding coordinating ligand, with the sample potentially containing the target multiple-charged biomolecule under conditions effective to allow the binding of the $d^8$ or $d^{10}$ metal complex to the target multiple-charged biomolecule by electrostatic interactions, and to allow subsequent self-assembly of a charged $d^8$ or $d^{10}$ metal complex aggregate, and (b) the measurement of the optical properties of the charged $d^8$ or $d^{10}$ metal complex aggregate.

The present invention further provides a kit for use in detecting a multiple-charged biomolecule in a sample comprising: (a) a composition that contains a charged $d^8$ or $d^{10}$ metal complex, wherein the metal complex electrostatically binds to the multiple charged biomolecule to induce aggregation and self-assembly of the $d^8$ or $d^{10}$ metal complex through metal-metal interactions and/or $\pi \ldots \pi$ interactions, and (b) instructions for use.

Table 1 shows some selected DNA oligonucleotides tested as illustrative examples.

Figure 8:
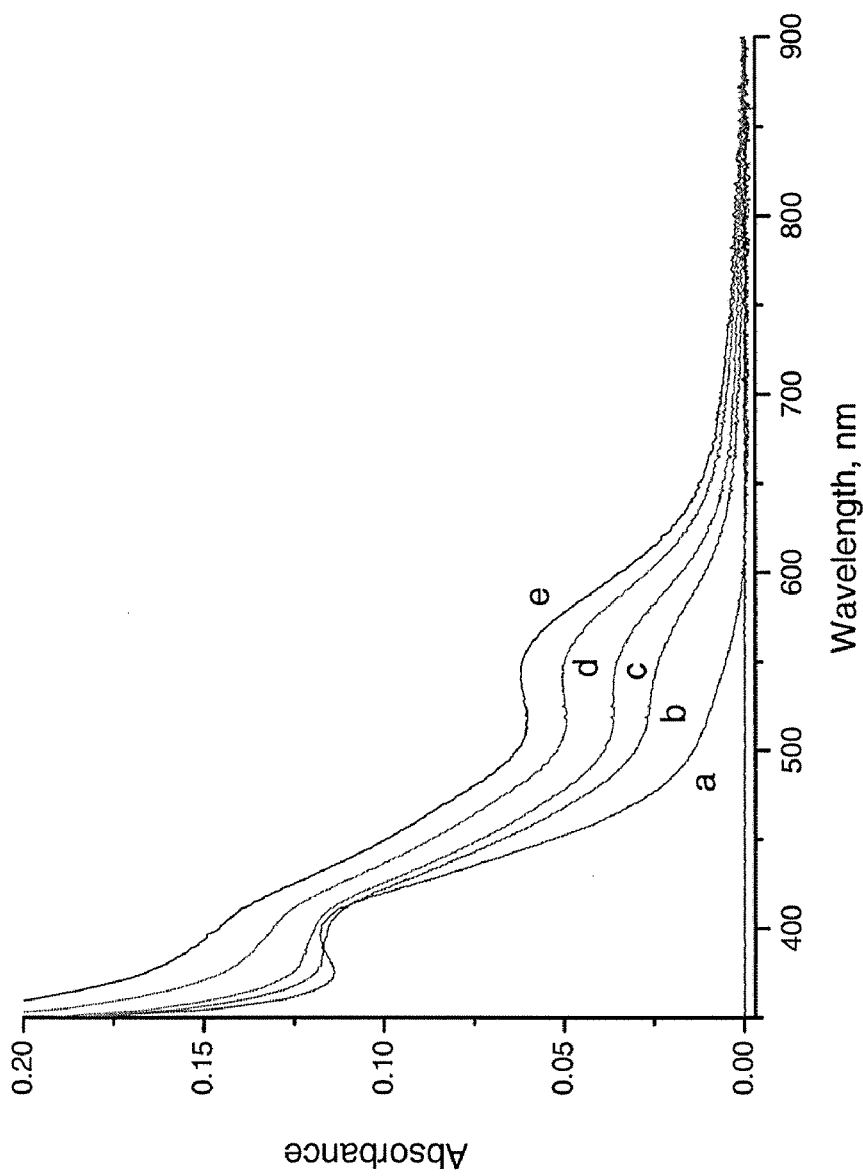

FIG. 8 shows the UV-Vis spectral changes indicating the formation of G-quadruplex structure and platinum complex self-assembly. Final concentration: 20 flM of oligonucleotide TGGG and 30 μM of complex 1 in the presence of 25 mM of NaCl (line a), 25 mM of 12-crown-4+25 mM of KCl (line b), 25 mM of 15-crown-5+25 mM of KCl (line c), 25 mM of 18-crown-6+25 mM of KCl (line d), and 25 mM of KCl (line e). Medium: 5 mMTris-HCl, pH 7.5, 20% trifluoroethanol.

Figure 9:
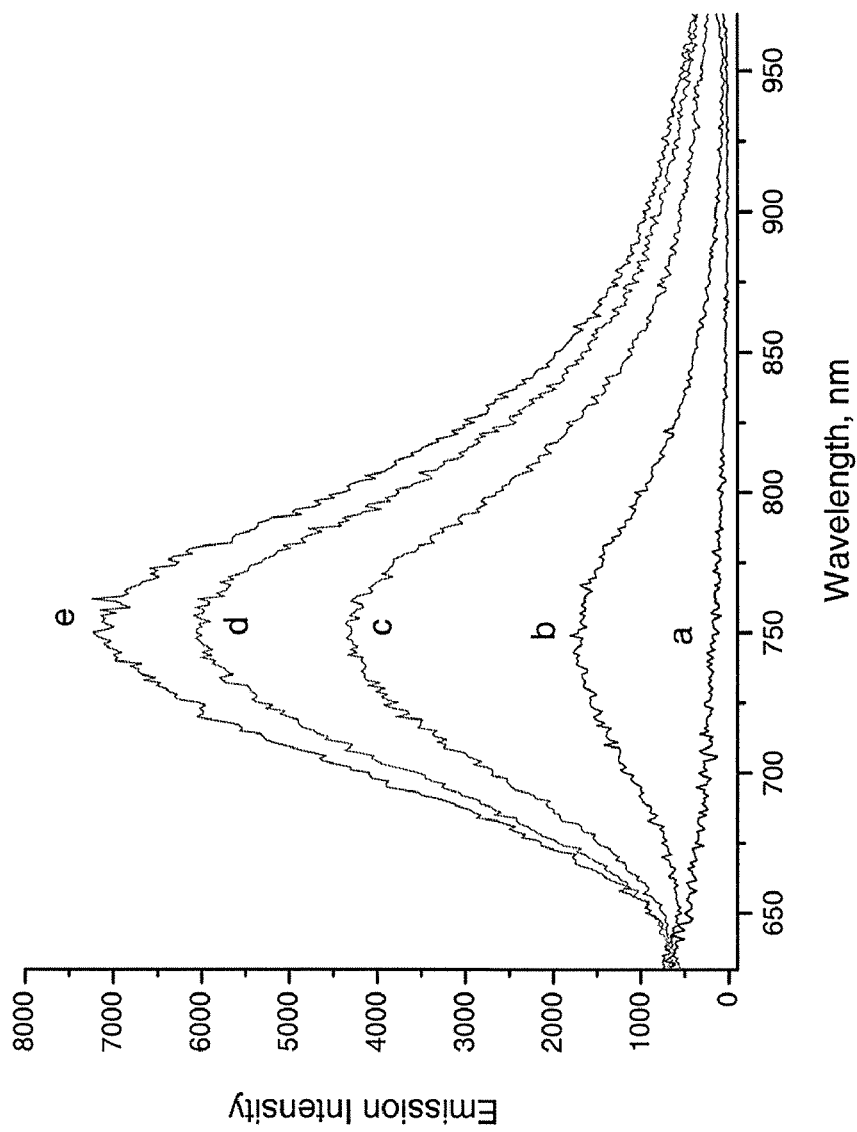

FIG. 9 shows the emission spectral changes indicating the formation of G-quadruplex structure and platinum complex self-assembly. Final concentration: 20 μM of oligonucleotide TGGG and 30 μM of complex 1 in the presence of 25 mM of NaCl (line a), 25 mM of 12-crown-4+25 mM of KCl (line b), 25 mM of 15-crown-5+25 mM of KCl (line c), 25 mM of 18-crown-6+25 mM of KCL (line d), and 25 mM of KCl (line e). Medium: 5 mM Tris-HCl, pH 7.5, 20% trifluoroethanol.

Figure 10:
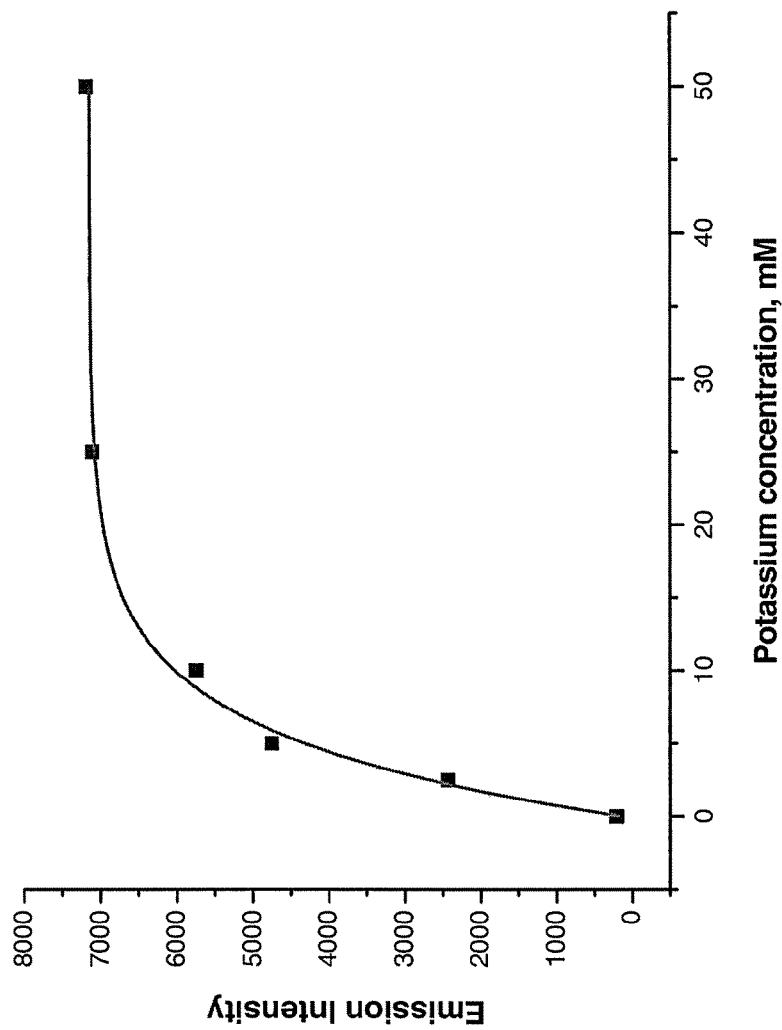

FIG. 10 shows the emission intensity changes at different K$^+$ concentrations. Final concentration: 20 μM of oligonucleotide TGGG and 30 μM of complex 1 in the presence of KCl. Medium: 5 mM Tris-HCl, pH 7.5, 20% trifluoroethanol.

Figure 11:
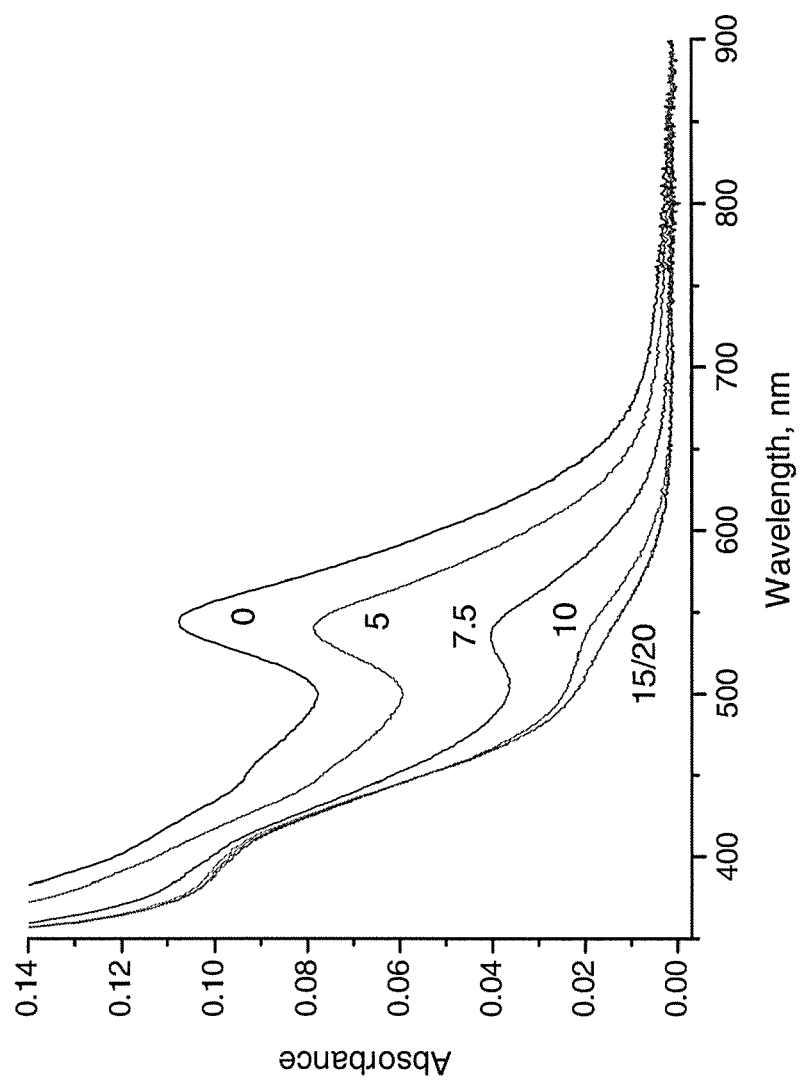

FIG. 11 shows the UV/vis spectral changes with time upon addition of 2 units of nuclease S1 to the mixture of complex 1 and poly(dT)$_{25}$. Experimental conditions: 148 μl H$_2$O+62 μl buffer (25 mM sodium acetate, 50 mM NaCl, 5 mM zinc sulphate, pH 4.6)+20 μl 1.62 mM of poly(dT)$_{25}$+10 μl nuclease S1 (1unit/5 μl), incubated for a specific period of time, followed by addition of 120 μl of 90 μM of complex 1.

Figure 12:
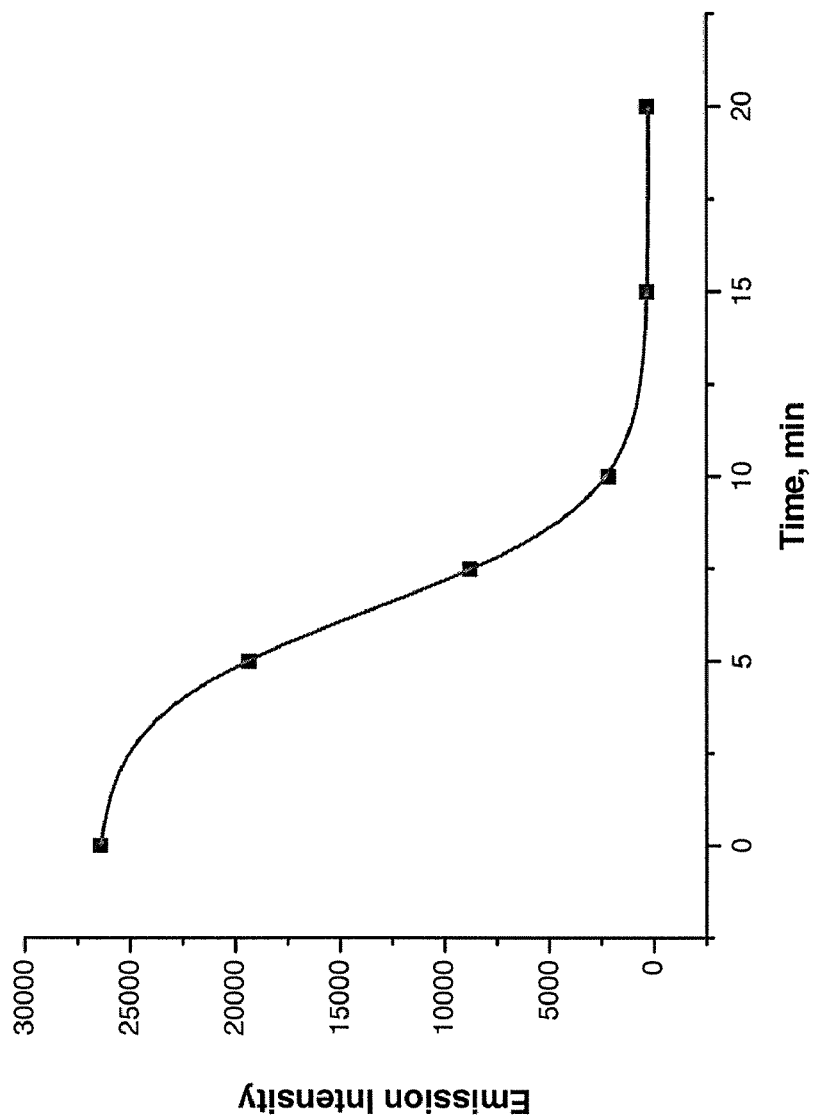

FIG. 12 shows the MMLCT emission intensity changes with time upon addition of 2 units of nuclease S1 to the mixture of complex 1 and poly(dT)$_{25}$. Experimental conditions: 148 μl H$_2$O+62 μl buffer (25 mM sodium acetate, 50 mM NaCl, 5 mM zinc sulphate, pH 4.6)+20 μl 1.62 mM of poly(dT)$_{25}$+10 μl nuclease S1 (1unit/5 μl), incubated for a specific period of time, followed by addition of 120 μl of 90 μM of complex 1.

DETAILED DESCRIPTION OF THE PREFERRED EMBODIMENTS

Definitions

As used in this application, except as otherwise expressly provided, each of the following terms shall have the meaning set forth below.

The term "single-stranded nucleic acid" employed herein can be single-stranded DNA, RNA of any length, natural or artificial, any derivatives or their analogues as long as it carries negative charge and the nucleic base sequence. It can be part of a duplex DNA or RNA, part of any combinations of DNA, RNA, protein, carbohydrate, lipid, and their derivatives. It may be freely distributed in solution, or immobilized onto a solid support surface. The nucleic acid can be directly obtained from a sample solution, or derived from amplified genes or gene fragments.

The term "biomolecule" employed herein can be DNA, RNA, protein, carbohydrate, lipid, their combinations and derivatives carrying multiple charges. It may be freely distributed in solution, or immobilized onto a solid support surface.

The term "charged" employed herein can be either anionic or cationic.

The term "charged d$^8$ or d$^{10}$ metal complex aggregate" employed herein can be any metal complex that contains at least one metal center of d$^8$ or d$^{10}$ electronic configuration that carries net positive or negative charge(s), which, in the vicinity of a biomolecule of opposite charge, can cause a local concentration enrichment of the metal complex, brought about by electrostatic interactions between the biomolecule and the metal complex.

The term "corresponding coordinating ligand" employed herein can be any donor ligand that forms a dative coordination bond to a metal center.

Embodiments of the Invention

The present invention provides a composition for detecting and/or characterizing a multiple-charged biomolecule comprising a charged d9 or d10 metal complex, wherein the metal complex electrostatically binds to the multiple charged biomolecule to induce aggregation and self-assembly of the metal complex through metal-metal interactions, π . . . π interactions, or a combination of both interactions.

In one embodiment, the charged d$^8$ or d$^{10}$ metal complex may comprise at least one transition metal and at least one corresponding coordinating ligand. A non-limiting list of examples of the transition metals contains platinum (Pt), gold (Au), palladium (Pd), rhodium (Rh), iridium (Ir), and silver (Ag), which are capable of participating in metal-metal interactions. A non-limiting list of examples of corresponding coordinating ligands contains aryl, alkyl, alkynyl, and their derivatives; nitrogen donor ligands including pyridine, bipyridine, terpyridine, polypyridine, arylpyridine, diarylpyridine, arylbipyridine, phenanthroline, diazine, triazine, phthalocyanine, imine, diimine, triimine, porphyrin, and their derivatives; sulfur, phosphorus, and oxygen donor ligands including phosphine, thiolate, carboxylate, and their derivatives. The corresponding coordinating ligand can also have the following structures:

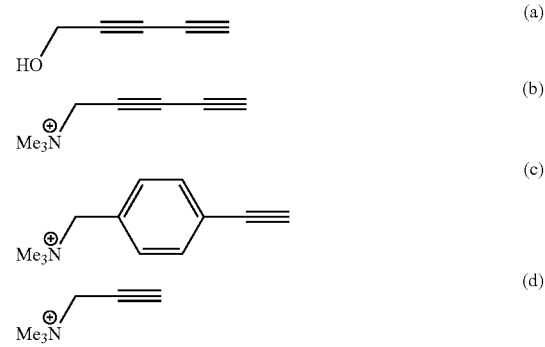

The charged $d^8$ or $d^{10}$ metal complex should carry at least one net positive or negative charge. Preferably, the metal complex has a planar structure or a partially planar structure, and at least one corresponding coordinating ligand is capable of $\pi \ldots \pi$ stacking interactions.

Preferably, the multiple-charged biomolecule should carry at least three net charges to induce the aggregation of the charged $d^8$ or $d^{10}$ metal complex.

The present invention also provides an assay method for detecting the presence or absence of a target multiple-charged biomolecule in a sample, which comprises: (a) the combination of a charged $d^8$ or $d^{10}$ metal complex, wherein the metal complex contains at least one transition metal and at least one corresponding coordinating ligand, with the sample potentially containing the target multiple-charged biomolecule under conditions effective to allow the binding of the $d^8$ or $d^{10}$ metal complex to the target multiple-charged biomolecule by electrostatic interactions, and to allow subsequent self-assembly of a charged $d^8$ or $d^{10}$ metal complex aggregate, and (b) the measurement of the optical properties of the charged $d^8$ or $d^{10}$ metal complex aggregate.

In one embodiment, the present invention provides a method for detecting the presence of a target single-stranded nucleic acid molecule in a sample solution. The target nucleic acid molecule can be analyzed directly, or can be amplified prior to the analysis. This method comprises the combining of a charged $d^8$ or $d^{10}$ metal complex with a sample solution potentially containing a target nucleic acid molecule, under conditions effective to allow at least one single-stranded nucleic acid to associate electrostatically with the $d^8$ or $d^{10}$ metal complex, and to allow subsequent self-assembly of the $d^8$ or $d^{10}$ metal complex; the determining of whether at least one single-stranded nucleic acid has electrostatically associated with the $d^8$ or $d^{10}$ metal complex, wherein self-assembly of the $d^8$ or $d^{10}$ metal complex, and subsequently the presence or absence of the target nucleic acid molecule, is indicated by changes in optical properties, such as in calorimetric assay, photoluminescence assay, or CD spectrometry analysis.

In another embodiment, the present invention provides a method for characterizing the structural properties of a target single-stranded nucleic acid. This method comprises the combining of a single-stranded nucleic acid molecule, of which the structural properties have been well-characterized, with a charged $d^8$ or $d^{10}$ metal complex, under conditions effective to allow at least one single-stranded nucleic acid to associate electrostatically with the $d^8$ or $d^{10}$ metal complex to form an associating complex; and to allow subsequent self assembly of the $d^8$ or $d^{10}$ metal complex, wherein self-assembly of $d^8$ or $d^{10}$ metal complex is recorded by changes in its optical properties, such as in colorimetric assay, photoluminescence assay, or CD spectrometry analysis. By conducting such experiments using different nucleic acid molecules of known structural properties, the combined set of information provides an effective way to deduce the structural properties of a target single-stranded nucleic acid.

In another embodiment, the present invention provides a method for detecting structural changes of a target single-stranded nucleic acid. This method can be carried out in two different ways. In one embodiment, the method comprises the combining of a target nucleic acid molecule with a charged $d^8$ or $d^{10}$ metal complex, under conditions effective to allow at least one single-stranded nucleic acid to associate electrostatically with the $d^8$ or $d^{10}$ metal complex to form an associating complex; and to allow subsequent self-assembly of the $d^8$ or $d^{10}$ metal complex, wherein self-assembly of d8 or d10 metal complex is recorded by changes in its optical properties, such as in colorimetric assay, photoluminescence assay, or CD spectrometry analysis. By conducting such experiments under different conditions, (e.g. different temperature, different ionic strength, or addition of compounds that may potentially cause structural property change of the target nucleic acid molecule), the optical properties are recorded, and changes in structural properties can then be deduced by comparing the changes in optical properties.

In a further embodiment, the method comprises the exposing of a target nucleic acid molecule to different conditions which may potentially induce structural property changes; the combining of the target nucleic acid molecule with a charged $d^8$ or $d^{10}$ metal complex, under conditions effective to allow at least one single-stranded nucleic acid to associate electrostatically with the $d^8$ or $d^{10}$ metal complex to form an associating complex; and to allow subsequent self-assembly of the $d^8$ or $d^{10}$ metal complex, wherein self-assembly of the $d^8$ or $d^{10}$ metal complex is recorded by changes in its optical properties, such as in colorimetric assay, photoluminescence assay, or CD spectrometry analysis. The recorded optical property changes can then be used to deduce the structural property changes of the target nucleic acid molecule.

In another embodiment, the present invention provides a method for detecting nucleic acid G-quadruplex formation in a sample solution. This method comprises the obtaining of a sample solution containing the target nucleic acid molecule; the exposing of the target nucleic acid to various conditions (e.g. different concentration, temperature, metal ions, etc.) which may potentially induce G-quadruplex formation; and then the exposing of the sample solution to a charged $d^8$ or $d^{10}$ metal complex under conditions effective to allow nucleic acid in the sample solution to electrostatically associate with the $d^8$ or $d^{10}$ metal complex to form associating complex; and to allow subsequent self-assembly of the $d^8$ or $d^{10}$ metal complex, wherein self-assembly of the $d^8$ or $d^{10}$ metal complex is recorded by changes in its optical properties, such as in colorimetric assay, photoluminescence assay, or CD spectrometry analysis; and the determining of whether the optical properties of the test solutions under various conditions are substantially different, which forms the basis for indicating the presence or absence of nucleic acid G-quadruplex formation of the target nucleic acid molecule.

In another embodiment, the present invention provides a method for detecting nucleic acid i-motif formation in a sample solution. This method comprises the obtaining of a sample solution containing the target nucleic acid molecule; the exposing of the target nucleic acid to various conditions (e.g. different concentration, temperature, metal ions, etc.) which may potentially induce i-motif formation; and then the exposing of the sample solution to a charged $d^8$ or $d^{10}$ metal complex under conditions effective to allow nucleic acid in the sample solution to electrostatically associate with the $d^8$ or $d^{10}$ metal complex to form associating complex; and to allow subsequent self-assembly of the $d^8$ or $d^{10}$ metal complex, wherein self-assembly of the $d^8$ or $d^{10}$ metal complex is recorded by changes in its optical properties, such as in colorimetric assay, photoluminescence assay, or CD spectrometry analysis; and the determining of whether the optical properties of the test solutions under various conditions are substantially different, which forms the basis for indicating the presence or absence of nucleic acid i-motif formation of the target nucleic acid molecule.

Figure 1:
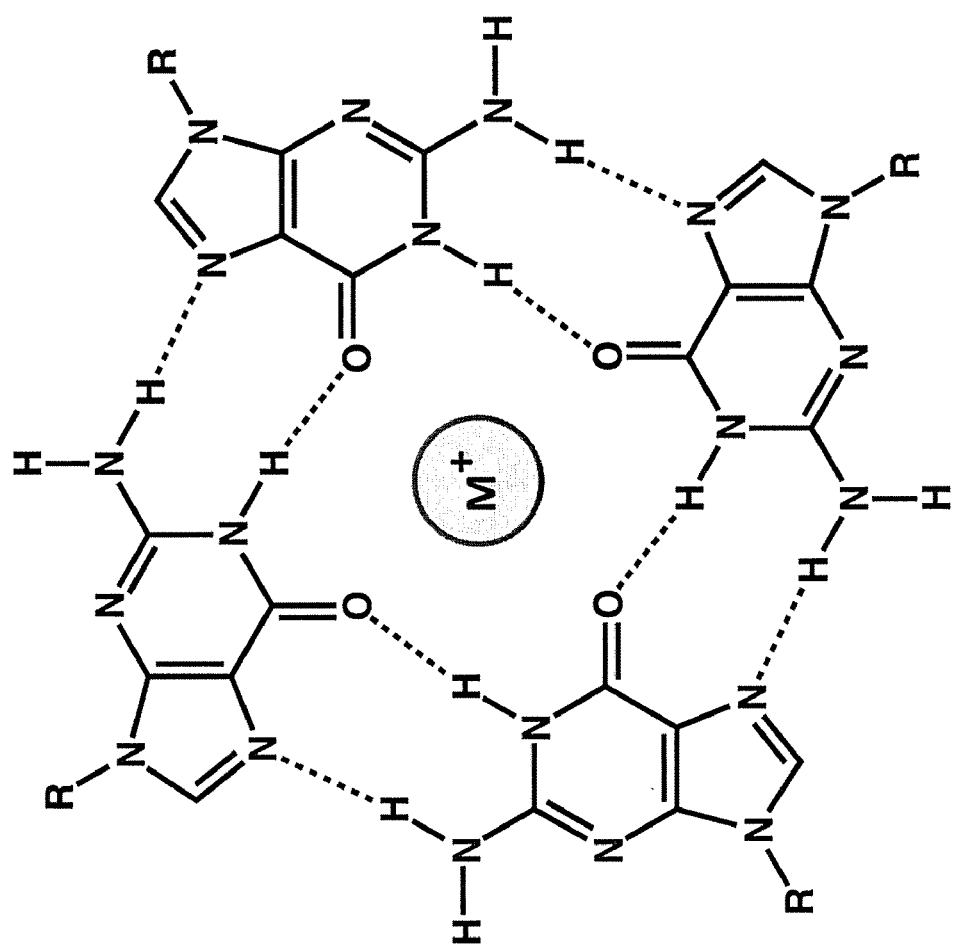
FIG. 1 shows the hydrogen bonding among four guanine bases in a G-quadruplex structure.

In another embodiment, the present invention provides a method for selectively detecting certain metal ions in a sample solution. The basis of this type of assay is that nucleic acid G-quadruplex formation is known to be promoted by the presence of certain monovalent cations, especially potassium ion. This happens by a coincidence of the size of potassium with the cavity created between two guanine quartets (FIG. 1). When a nucleic acid which can potentially form G-quadruplex is mixed with certain concentration of a metal ion (e.g. potassium ion), and if the metal ion concentration is high enough, nucleic acid G-quadruplex will form and consequently significant complex self-assembly will be observed; if the metal ion concentration is too low, no quadruplex formation occurs and thus no complex self-assembly will be observed; and if the metal ion concentration is anywhere in between, a certain degree of quadruplex formation will be observed, which is related to the metal ion concentration.

The method comprises obtaining a sample solution containing an appropriate nucleic acid molecule, which can potentially form a G-quadruplex structure under certain concentration of the metal ion (e.g. potassium); combining the nucleic acid with various concentrations of the metal ion, under conditions which favor G-quadruplex formation; exposing the sample solution to a charged $d^8$ or $d^{10}$ metal complex under conditions effective to allow the nucleic acid in the sample solution to electrostatically associate with the $d^8$ or $d^{10}$ metal complex to form an associating complex, and allowing subsequent self-assembly of the $d^8$ or $d^{10}$ metal complex, wherein self-assembly of the $d^8$ or $d^{10}$ metal complex is identified by changes in its optical properties, such as in a colorimetric assay, a photoluminescence assay, or a CD spectrometry analysis; and determining whether the optical property changes are associated with the concentration of the metal ion, which indicates the presence or absence of certain concentration of metal ion in the sample solution.

In another embodiment, the present invention provides a method for label-free, and real-time monitoring of enzymatic cleavage of single-stranded nucleic acid. The assay method is based on the following: (a) in the presence of longer oligonucleotides, the $d^8$ or $d^{10}$ metal complexes will form helical self-assembly, which can be easily monitored by UV/vis, emission, and CD spectroscopy; (b) when the oligonucleotides are mostly cleaved, only short oligonucleotides are available (with length≦5 nucleic acid bases), and no complex self-assembly can be formed, and thus no spectroscopic changes can be detected; (c) when the oligonucleotides are only partially enzymatically cleaved, reduced spectroscopic changes can be detected.

The method comprises obtaining a sample solution containing an appropriate nucleic acid molecule; adding a nuclease to the sample solution, with conditions effective to allow cleavage of the nucleic acid by the nuclease; exposing the sample solution to a charged $d^8$ or $d^{10}$ metal complex under conditions effective to allow nucleic acid in the sample solution to electrostatically associate with the $d^8$ or $d^{10}$ metal complex to form associating complex; and allowing the subsequent self-assembly of the $d^8$ or $d^{10}$ metal complex, wherein self-assembly of the $d^8$ or $d^{10}$ metal complex is identified by changes in its optical properties, such as in a colorimetric assay, a photoluminescence assay, or a CD spectrometry analysis; and determining whether there are any optical property changes, which indicate the presence or absence of nuclease activity in the sample solution.

In another embodiment, the present invention provides a method for monitoring nucleic acid radical damage. The assay method is based on the same principle as the one for monitoring nucleic acid enzymatic cleavage: (a) in the presence of longer oligonucleotides, the $d^8$ or $d^{10}$ metal complexes will form helical self-assembly, which can be easily monitored by UV/vis, emission, and CD spectroscopy; (b) when the oligonucleotides are seriously damaged by reactive radicals, it will break into pieces, and therefore only short oligonucleotides are available (with length≦5 nucleic acid bases), and no complex self-assembly can be formed, thus no spectroscopic changes can be detected; and (c) when the oligonucleotides are only partially damaged, reduced spectroscopic changes can be detected.

As an illustrative example, the hydroxyl radicals can be generated by a commonly used Fenton's reagent:

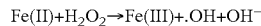

$$Fe(II)+H_2O_2 \rightarrow Fe(III)+\cdot OH+OH^-$$

The method comprises obtaining of a sample solution containing an appropriate nucleic acid molecule; combining the nucleic acid solution and a solution containing reactive radicals (the radicals can be freshly generated before adding to the nucleic acid solution, or generated in situ by subsequent addition of key radical generating components); exposing the sample solution to a charged $d^8$ or $d^{10}$ metal complex under conditions effective to allow the nucleic acid in the sample solution to electrostatically associate with the $d^8$ or $d^{10}$ metal complex to form associating complex, and allowing the subsequent self-assembly of the $d^8$ or $d^{10}$ metal complex, wherein self-assembly of the $d^8$ or $d^{10}$ metal complex is recorded by changes in its optical properties, such as in colorimetric assay, photoluminescence assay, or CD spectrometry analysis; and determining whether there is any optical property changes, which forms the basis for indicating the presence or absence of radical nucleic acid damage.

The present invention further provides kits containing various components that will allow users to perform one or more aforementioned methods of the present invention. Specifically, the present invention further provides a kit for use in detecting a multiple-charged biomolecule in a sample comprising: (a) a composition that contains a charged d8 or d10 metal complex, wherein the metal complex electrostatically binds to the multiple-charged biomolecule to induce aggregation and self-assembly of the $d^8$ or $d^{10}$ metal complex through metal-metal interactions and/or π . . . π interactions, and (b) instructions for use.

The present invention further provides kits containing various components that will allow users to perform the monitoring of processes (such as substrate binding) or activities (such as enzymatic reactions) that will convert multiple charged biomolecules or molecules to their uncharged forms, or from their uncharged forms to multiple-charged species, via a change in the electrostatic binding to induce self-assembly of the $d^8$ or $d^{10}$ metal complexes through metal-metal interactions and/or π . . . π interactions, that is recorded as changes in its optical properties, such as in colorimetric assay, photoluminescence assay, or CD spectrometry analysis.

The kits minimally include a first container that contains a solution of the charged $d^8$ or $d^{10}$ metal complex, which can be cationic or anionic, and a second container that contains an aqueous solution including at least one multiple-charged biomolecule carrying at least three net charges that are opposite in charge to that of the $d^8$ or $d^{10}$ metal complex.

EXAMPLES

The following examples are provided to illustrate embodiments of the present invention, and are by no means intended to limit the scope of the present invention. Those skilled in the art will recognize that various changes and modifications can be made in the present invention without departing from its spirit and scope.

Example 1

Representative Examples of the $d^8$ or $d^{10}$ Metal Complex

Figure 2:
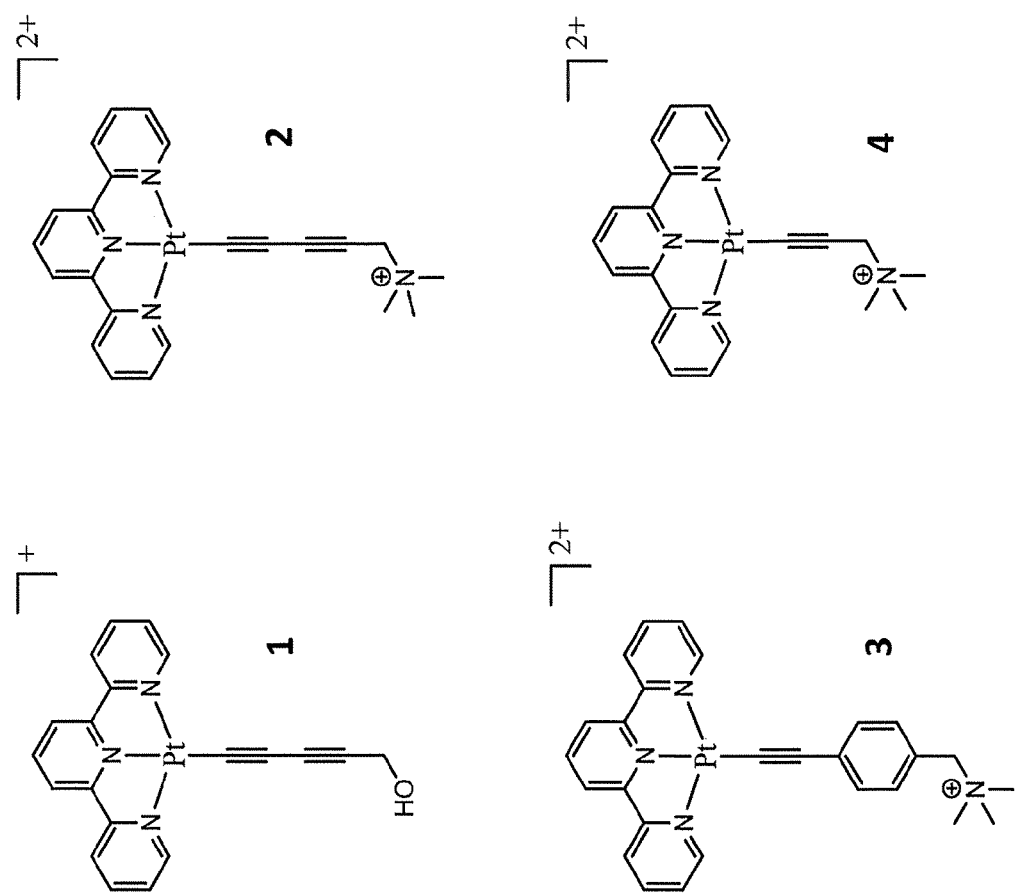
FIG. 2 shows the structure of four cationic $d^8$ metal complexes as illustrative examples.
Figure 3:
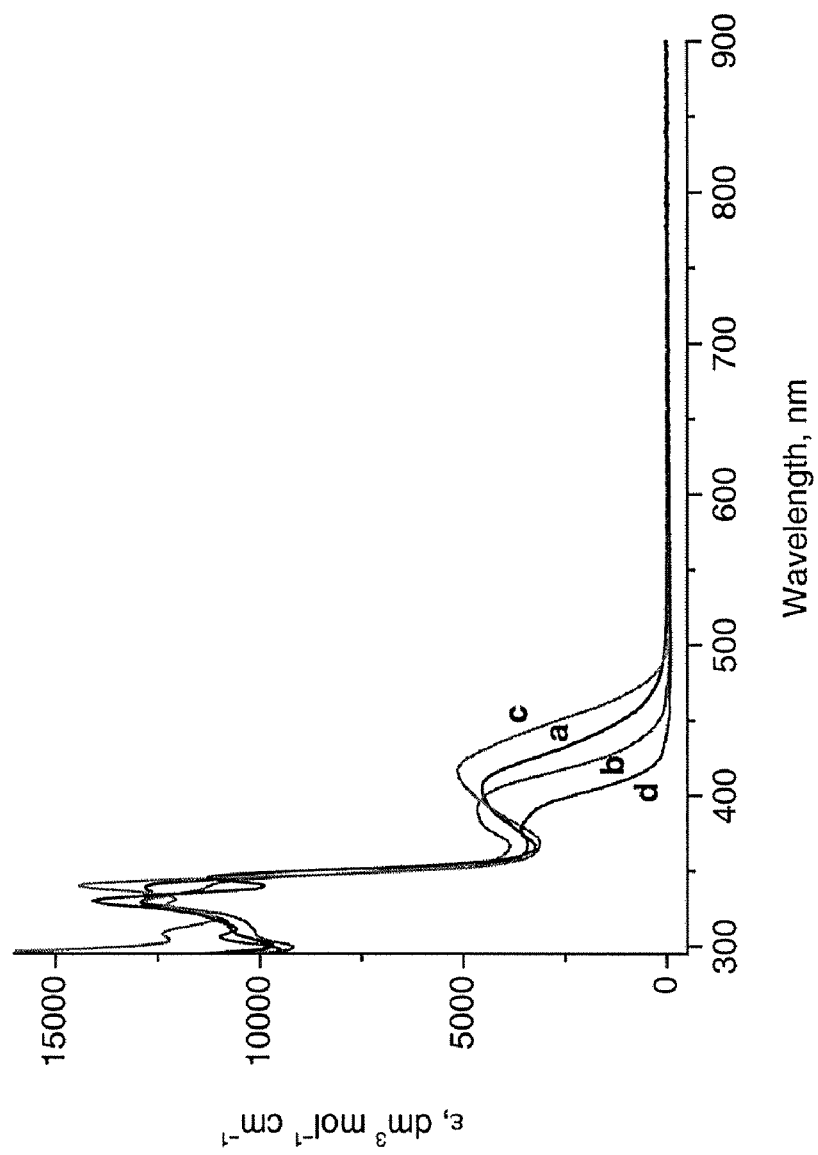
FIG. 3 shows the overlaid UV-vis spectra of 30 μM of complexes in buffer-MeCN solvent mixture (curves a-d for complexes 1-4 respectively. Medium: 5 mM Tris-HCl, 10 mM NaCl, pH 7.5, 40% MeCN).

Four examples of the metal complexes are provided (FIG. 2). They were either prepared by existing literature methods which are known by those skilled in the art, or prepared via the synthetic routes given in reference 51. All the metal complexes have certain properties that are especially suitable for the aggregation studies described in the present invention. All complexes contain a metal center (Pt), which is a d8 transition metal ion and capable of participating in metal-metal interactions. They also contain aromatic terpyridine ligand that can interact with each other by π . . . π stacking interactions. Of the four complexes, complex 3 which contains an extra phenyl ring is the most hydrophobic. For complexes 2-4, the positively charged trimethylammonium group is furthest away from the platinum metal center and the terpyridine ligand in 3, while complex 4, which contains only one alkynyl unit, has the positively charged trimethylammonium group closest in distance to the platinum metal center and the terpyridine ligand. Complex 1 contains one positive charge and a hydroxyl functional group, whereas complexes 2-4 contain two net positive charges, as a result, these complexes are rather soluble in water.

Example 2

Figure 4:
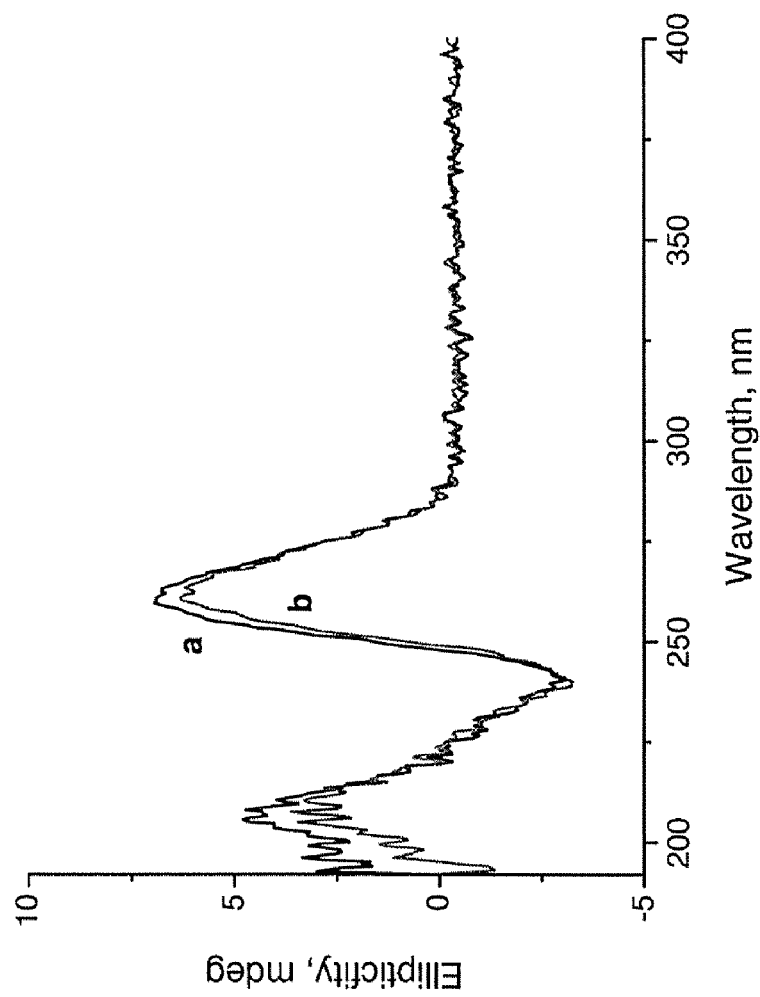
FIG. 4 shows the overlaid CD spectra of one of the representative single-stranded nucleic acids, 90 μM of poly(dG)$_{25}$ (line a), and spectral changes thereof upon binding to a d$^8$ metal complex, 30 μM of complex 1 (line b).

Binding of the $d^8$ Metal Complex 1 shown in FIG. 2 to G-Quadruplex DNA Structure Studied by UV/Vis, Emission, and CD Spectroscopy Our studies show that when poly$(dG)_{25}$ was mixed with complex 1, as expected, good complex self-assembly was observed (50). Interestingly, the CD spectrum of poly$(dG)_{25}$ mixed with complex 1 shows little changes (FIG. 4). The changes in optical properties of the metal complexes when mixed with poly$(dG)_{25}$ were apparently associated with the primary and secondary structure of the oligonucleotide. CD spectrum of poly$(dG)_{25}$ showed characteristic peaks which suggested the formation of G-quadruplex structure (22), a result of hydrogen bonding and base stacking interactions among guanine bases. As a result, the complex self-assembly was not helical.

Example 3

Figure 5:
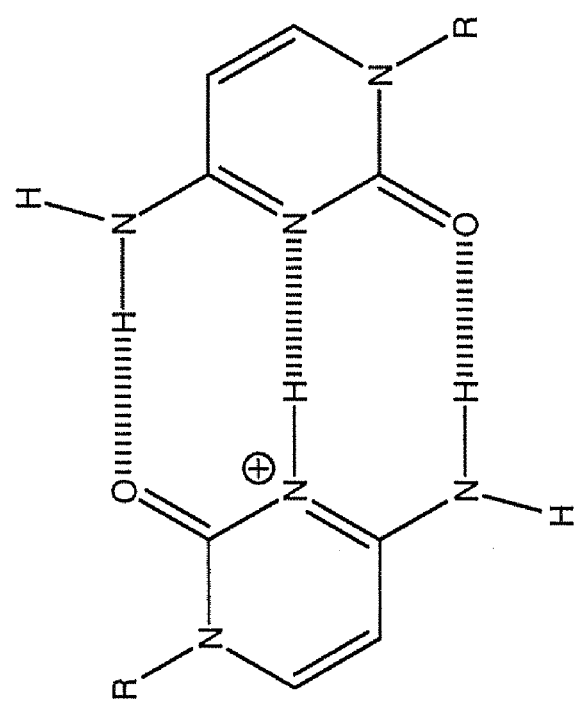
FIG. 5 shows the hydrogen bonding in cytosine-protonated cytosine (C—C$^+$) base pair.
Figure 6:
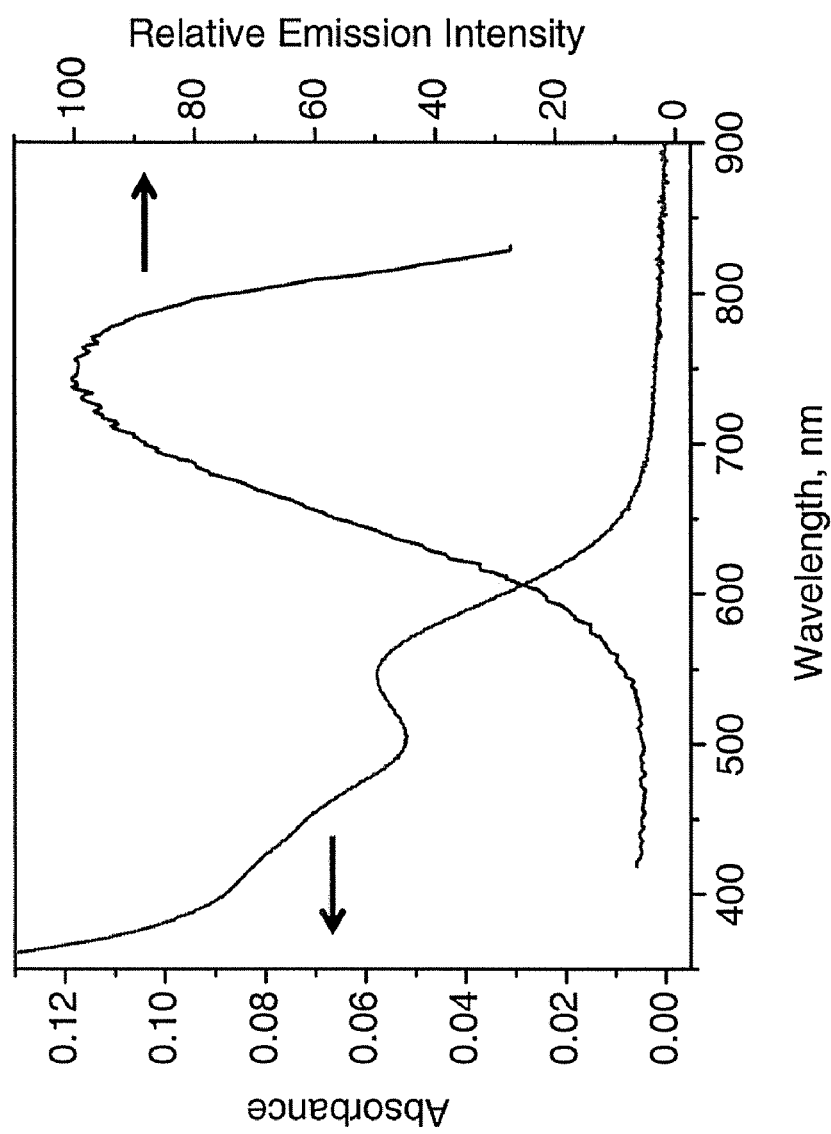
FIG. 6 shows the overlaid UV-vis absorption and emission spectra of 90 μM of poly(dC)$_{25}$+30 μM of complex 1. Medium: 5 mM HOAc-NaOAc, 10 mM NaCl, pH 5.0.
Figure 7:
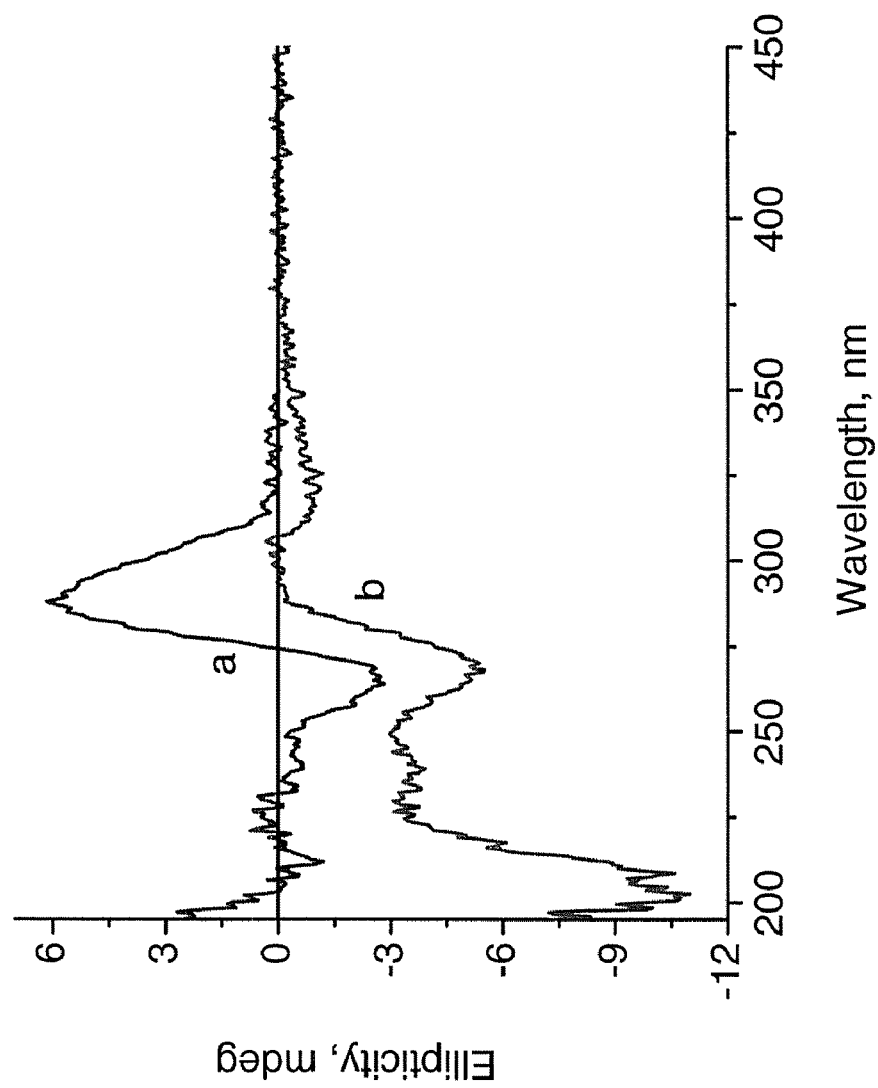
FIG. 7 shows the overlaid CD spectra of 90 μM of poly (dC)$_{25}$ (line a), and its binding with 30 μM of complex 1 (line b). Medium: 5 mM HOAc-NaOAc, 10 mM NaCl, pH 5.0.

Binding of the $d^8$ Metal Complex 1 shown in FIG. 2 to i-Motif DNA Structure Studied by UV/Vis, Emission, and CD Spectroscopy Although poly(dC) is known to adopt a helical conformation under basic conditions, under acidic conditions, poly(dC) forms the very unique i-motif structure, as a result of the C—$C^+$ (cytosine-protonated cytosine) base paring (FIG. 5). At pH 5.0, improved self-assembly of complex 1 was observed when mixed with poly$(dC)_{25}$, as revealed by the enhancement of the MMLCT bands in both the UV-vis and the emission spectra (FIG. 6). However, the CD spectrum induced by metal complex binding is found to be quite different from the helical assembly obtained previously, and also different from the CD signatures of the i-motif structure (FIG. 7), that was initially formed before metal complex binding. The very compact i-motif structure appears to facilitate the self-assembly of the complex cations, albeit different from the helical assembly as revealed by the CD.

Example 4

Binding of Complex 1 shown in FIG. 2 to Oligonucleotides, G-Quadruplex Formation and the Selective Label-Free Sensing of Potassium Ion It was found during our detailed investigation that the induced complex self-assembly was dependent on the chain length of the single-stranded oligo oligonucleotide. With only five nucleotide units, little induced complex self-assembly was observed, when the oligonucleotide contained ten or more nucleotide units, significant complex self-assembly was observed. We speculate that since a G-quadruplex contains four DNA strands, for one individual strand, if the number of nucleotide units is equal or less than five, no induced complex self-assembly should be observed, and when four oligonucleotides aggregate to form a quadruplex structure, the number of nucleotide units in each quadruplex structure easily exceeds ten, and induced complex self-assembly should be observed. The induced complex self-assembly therefore could be used for the detection of DNA G-quadruplex formation. More importantly, since it was generally observed that the G-quadruplex structure is better stabilized by potassium ion than any other metal ions, the present approach could possibly be used for the specific sensing of potassium ion. Because of the involvement of potassium ion in many biological processes, an approach that could be used to specifically sense potassium against other metal ions is of obvious importance.

Several short DNA oligonucleotides for G-quadruplex formation are tested in this study (Table I). In an aqueous solution with constant pH and ionic strength {5 mM Tris. HCl/10 mM NaCl, pH 7.5, 20% trifluoroethanol (TFE)} at ambient temperature, spectral changes of the mixture of complex 1 with various preformed DNA G-quadruplexes by addition of potassium ion are investigated. It is found that the DNA oligonucleotide TGGG gives the best performance from the result of remarkable spectroscopic changes. For TGGG DNA oligonucleotide, when mixed with platinum(II) complex and using $K^+$ as the stabilizing ion, formation of new absorption band occurs at ca. 550 nm as indicated in FIG. 8. Concomitant with the remarkable UV-vis absorption changes, a low-energy emission emerges in the NIR region upon mixing of the complex with the described G-quadruplex (FIG. 9). In the presence of $K^+$, oligonucleotide TTAGGG (human telomeric DNA repeat) induces a much smaller degree of complex self-assembly (peak intensity, 18% of that induced by TGGG) while other tested oligonucleotides give little induced complex self-assembly. On the basis of our previous work and other related studies, the newly formed absorption bands at longer wavelength are attributed to metal-metal to ligand charge transfer MMLCT transitions, as a result of the self assembly of the complexes induced by the G-quadruplex through metal-metal and π . . . π interactions. The newly formed emission bands are assigned as 3MMLCT emission. Owing to the electrostatic interaction between the multinegatively charged G-quadruplex and positively charged platinum (II) complex, these two species tend to come into close proximity, i.e., binding of the complex molecules to the bio-oligomer. Thus, the increased local concentration of the complex and charge neutralizations upon the binding process facilitate the self-association and aggregation of the planar complex molecules and give rise to the remarkable spectroscopic changes. As a result, G-quadruplex formation could be detected via the self-assembly of platinum (II) complex in our optimized conditions.

The variation of $K^+$ ion concentration used in G-quadruplex formation is studied by emission spectroscopy. The results show that the intensity of the induced complex $^3$MMLCT emission increases with the increase of $K^+$ ion concentration, and further increase of the $K^+$ ion concentration from 25 mM to 50 mM only causes little spectral enhancement in our studies. FIG. 10 shows the emission intensity changes at the NIR region upon varying the $K^+$ concentration of the TGGG DNA oligo and complex mixture.

In sharp contrast, 50 mM of NaCl causes no induced complex self-assembly, and consequently no UV-vis and emission MMLCT bands are observed (FIGS. 8 and 9). Addition of higher concentrations of Na⁺ were performed, and the results show that even at 100, 200, 300, 400 mM Na⁺ concentration, no detectable aggregation signals could be found in the absorption and emission studies. Besides Na⁺, other commonly present metal ions, such as $Li^+$, $Ca^{2+}$, and $Mg^{2+}$ were also tested (Cl as counter ion in all cases). It is found that negative responses are observed for adding 50 mM of these metal ions. The results strongly suggest that the present approach can sense the presence of potassium ion very selectively by G-quadruplex induced complex self-assembly.

It is well known that certain crown ethers can bind positively charged metal ions. With a few exceptions, the selectivity of the crown ethers is usually modest. Because the size of the central cavity of the host would determine the guest it binds, different metal ions would preferably bind to specific crown ethers, i.e. $Li^+$, $Na^+$, and $K^+$ preferably bind 12-crown-4, 15-crown-5, and 18-crown-6 respectively. Therefore, attempts to add different crown ethers into the assay solution in order to investigate the competition of potassium ion between the quadruplex and crown ethers were performed (FIGS. 8 and 9). When 18-crown-6 was added to the assay solution, large spectroscopic changes are observed. It shows that the absorption and emission intensity of the MMLCT band was largely reduced upon adding the 18-crown-6. As 15-crown-5 and 12-crown-4 are added, similar but smaller spectroscopic changes are found in both cases and 12-crown-4 exerts the least effect on the diminishment of MMLCT band intensities. The results indicate that binding of the crown ether with the potassium ion will compete with binding of the potassium ion to the G-quadruplex, that will reduce the extent of G-quadruplex formation and the complex self-assembly, consequently reduce the UV-vis and emission band intensity.

Example 11

Binding of Complex 1 shown in FIG. 2 to Oligonucleotides, Sensing of Nucleic Acid Enzymatic Cleavage Our new assay method is based on the following facts: (a) in the presence of longer oligonucleotide, the $d^8$ or $d^{10}$ metal complexes will form helical self-assembly, which could be easily monitored by UV/vis, emission, and CD spectroscopy; (b) when the oligonucleotide is cleaved, only short oligonucleotides are available (with length≦5 nucleic bases), and no complex self-assembly could be formed, thus no spectroscopic changes could be detected. FIG. 11 (UV/vis) shows the decrease of complex self-assembly with time in the presence of poly(dT)$_{25}$ and 2 units of nuclease S1. FIG. 12 shows the decrease of MMLCT emission intensity with time in the presence of poly(dT)$_{25}$ and 2 units of nuclease S1.

References

The following are incorporated by reference herein:
1. U.S. Pat. No. 5,985,567, issued Nov. 16, 1999 (Rampal).
2. U.S. Pat. No. 6,132,972, issued Oct. 17, 2000 (Shigemori et al.).
3. U.S. Published Patent Application No. US20050059042, published Mar. 17, 2005 (Rothberg).
4. U.S. Publication Application No. US20040219556, published Nov. 4, 2004 (Bazan).
5. U.S. Publication Application No. US20040033518, published Feb. 19, 2004 (Wittwer).
6. U.S. Publication Application No. US20050048485, published Mar. 3, 2005 (Kurane).
7. U.S. Publication Application No. US20010046670, published Nov. 29, 2001 (Brookes).
8. PCT International Publication No. WO2004111602, published Dec. 23, 2004 (Rothberg).
9. PCT International Publication No. WO03091408, published Nov. 6, 2003 (Wittwer).
10. PCT International Publication No. WO9846790, published Oct. 22, 1998 (Harbron).
11. PCT International Publication No. WO9942616, published Aug. 26, 1999 (Patel).
12. Canadian Patent Application No. CA2489922, filed Jun. 20, 2003 (Gaylord, B. and Bazan, G.).
13. British Patent No. GB2318791, issued May 6, 1998 (Charles).
14. Japanese Patent No. JP 1151100, issued Jun. 8, 1999 (Shigemori).
15. Japanese Patent No. JP61219400, issued Sep. 29, 1986 (Yokota).
16. KOKAI Open Application No. JP2005000088, published Jan. 6, 2005 (Shigemori).
17. Adamovich et al., "High Efficiency Single Dopant White Electrophosphorescent Light Emitting Diodes," New Journal of Chemistry, 2002, 26, 1171-1178.
18. Backburn et al. ed., "Nucleic Acids in Chemistry and Biology", Oxford University Press, Oxford, 1996.
19. Bailey et. al., "Electronic Spectroscopy of Chloro(terpyridine)platinum(II)" Inorganic Chemistry, 1995, 34, 4591-4599.
20. Bloomfield et al., "Nucleic Acids: Structures, Properties, and Functions," University Science Books, California, 2000.
21. Creighton, "Proteins: Structure and Molecular Properties", W. H. Freeman and Company, New York, 1993.
22. Fasman ed., "Circular Dichroism and the Conformational Analysis of Biomolecules," Plenum Press, New York, 1996.
23. Gaylord et al., "DNA Detection Using Water-Soluble Conjugated Polymers and Peptide Nucleic Acid Probes", Proceedings of the National Academy of Sciences of the United States of America, 2002, 99, 10954-10957.
24. Goshe et al., "Supramolecular Recognition. Terpyridyl Palladium and Platinum Molecular Clefts and Their Association with Planar Platinum Complexes", Journal of the American Chemical Society, 2003, 125, 444-451.
25. Han et al., "Interactions of TMPyP4 and TMPyP2 with Quadruplex DNA. Structural Basis for the Differential Effects on Telomerase Inhibition," Journal of the American Chemical Society, 1999, 121, 3561-3570.
26. Herber et al., "Origin of Polychromism of Cis Square-Planar Platinum(II) Complexes: Comparison of Two Forms of [Pt(2,2'-bpy)(Cl)₂]," Inorganic Chemistry, 1994, 33, 2422-2426.
27. Houlding et. al., "The effect of linear chain structure on the electronic structure of platinum(II) diimine complexes," Coordination Chemistry Reviews, 1991, 111, 145-152.
28. Hill et. al., "Spectroelectrochemistry and Dimerization Equilibria of Chloro(terpyridine)platinum(II). Nature of the Reduced Complexes," Inorganic Chemistry, 1996, 35, 4585-4590.
29. Towbin et. al., "Clinical Implications of Basic Research; New Revelations about the Long-QT Syndrome," New England Journal of Medicine, 1995, 333, 384-385.
30. Jennette et. al., "Metallointercalation Reagents. 2-Hydroxyethanethiolato (2,2',2"-terpyridine)platinum(II)

30. Monocation Binds Strongly to DNA by Intercalation," Proceedings of the National Academy of Sciences of the United States of America, 1974, 71, 3839-3843.
31. Mitcheson et. al., "A Structural Basis for Drug-Induced Long QT Syndrome," Proceedings of the National Academy of Sciences of the United States of America, 2000, 97, 12329-12333.
32. Kakar et. al., "Reconstitution of the Mitochondrial Non-Selective Sodium/Hydrogen Ion (Potassium/Hydrogen Ion) Antiporter into Proteoliposomes," Journal of Biological Chemistry, 1989, 264, 5846-5851.
33. Kang et. al., "Crystal Structure of Four-Stranded Oxytricha Telomeric DNA," Nature, 1992, 356, 126-131.
34. Keating et. al., "Molecular and Cellular Mechanisms of Cardiac Arrhythmias," Cell, 2001, 104, 569-580.
35. Laughlan et. al., "The High-Resolution Crystal Structure of a Parallel-Stranded Guanine Tetraplex," Science, 1994, 265, 520-524.
36. Li et al., "Label-Free Colorimetric Detection of Specific Sequence in Genomic DNA by the Polymerase Chain Reaction," Journal of the American Chemical Society, 2004, 126, 10958-10961.
37. Lippard, "Platinum Complexes: Probes of Polynucleotide Structure and Antitumor Drugs," Accounts of Chemical Research, 1978, 11, 211-217.
38. Miller J S, (ed.), (1982) *Extended Linear Chain Compounds, Vol. 1* (Plenum Press, New York).
39. Nagatoishi et. al., "A Pyrene-Labeled G-Quadruplex Oligonucleotide as a Fluorescent Probe for Potassium Ion Detection in Biological Applications," Angewandte Chemie International Edition, 2005, 44, 5067-5070.
40. Nagatoishi et. al., "G Quadruplex-Based FRET Probes with the Thrombin-Binding Aptamer (TBA) Sequence Designed for the Efficient Fluorometric Detection of the Potassium Ion," ChemBioChem, 2006, 7, 1730-1737.
41. Recanatini et. al., "QT Prolongation Through HERG K$^+$ Channel Blockade: Current Knowledge and Strategies for the Early Prediction During Drug Development," Medicinal Research Reviews, 2005, 25, 133-166.
42. Sanguinetti et. al., "hERG Potassium Channels and Cardiac Arrhythmia," Nature, 2006, 440, 463-469.
43. Sen et. al., "A Sodium-Potassium Switch in the Formation of Four-Stranded G4-DNA," Nature, 1990, 344, 410-414.
44. Williamson et. al., "Monovalent Cation-Induced Structure of Telomeric DNA: The G-Quartet Model," Cell, 1989, 59, 871-880.
45. Yam et al., "Synthesis, Luminescense, Electrochemistry, and Ion-Binding Studies of Platinum(II) Terpyridyl Acetylide Complexes," Organometallics, 2001, 20, 4476-4482.
46. Yam et al., "Solvent-Induced Aggregation through Metal . . . Metal/π . . . π Interactions: Large Solvatochromism of Luminescent Organoplatinum(II) Terpyridyl Complexes," Journal of the American Chemical Society, 2002, 124, 6506-6507.
47. Yam et al., "Luminescent Platinum(II) Terpyridyl Complexes: Effect of Counter Ions on Solvent-Induced Aggregation and Color Changes," Chemistry—A European Journal, 2005, 11, 4535-4543.
48. Yip et. al., "Luminescent platinum(II) Complexes. Electronic Spectroscopy of Platinum(II) Complexes of 2,2':6', 2"-Terpyridine (terpy) and p-Substituted Phenylterpyridines and Crystal Structure of [Pt(terpy)Cl][CF$_3$SO$_3$]," Journal of the Chemical Society, Dalton Transtractions, 1993, 2933-2938.
49. Yu et al., "Polymer-Induced Self-Assembly of Alkynylplatinum(II) Terpyridyl Complexes by Metal . . . Metal/π . . . π Interactions," Angewandte Chemie International Edition, 2005, 44, 791-794.
50. Yu et al., "Single-Stranded Nucleic Acid-Induced Helical Self-Assembly of Alkynylplatinum(II) Terpyridyl Complexes," Proceedings of the National Academy of Sciences of the United States of America, 2006, 103, 19652-19657.
51. Yu et al., "Polyelectrolyte-Induced Self-Assembly of Positively Charged Alkynylplatinum(II) Terpyridyl Complexes in Aqueous Media," Manuscript submitted.
52. Ueyama, H.; Takagi, M.; Takenaka, S. "A Novel Potassium Sensing in Aqueous Media with a Synthetic Oligonucleotide Derivative. Fluorescence Resonance Energy Transfer Associated with Guanine Quartet-Potassium Ion Complex Formation," J. Am. Chem. Soc. 2002, 124, 14286.

What is claimed is:

1. A composition for detecting or characterizing nucleic acid enzymatic cleavage comprising a charged $d^8$ or $d^{10}$ metal complex, wherein the charged $d^8$ or $d^{10}$ metal complex electrostatically binds to a multiple-charged biomolecule to induce aggregation and self-assembly of the metal complex through metal-metal interactions, π . . . π interactions, or a combination of both interactions, and wherein the metal complex comprises at least one transition metal, at least one carbon donor ligand, and at least one corresponding coordinating ligand; and wherein the carbon donor ligand has one of the following structures:

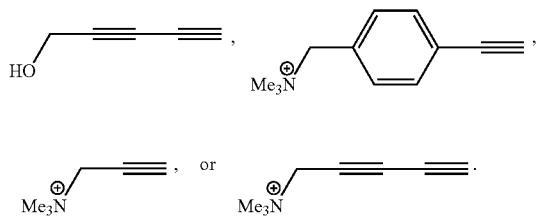

2. A composition for detecting or characterizing nucleic acid radical damage comprising a charged $d^8$ or $d^{10}$ metal complex, wherein the charged $d^8$ or $d^{10}$ metal complex electrostatically binds to a multiple-charged biomolecule to induce aggregation and self-assembly of the metal complex through metal-metal interactions, π . . . π interactions, or a combination of both interactions, and wherein the metal complex comprises at one least transition metal, at least one carbon donor legend, and at least one corresponding coordinating ligand; and wherein the carbon donor ligand has one of the following structures:

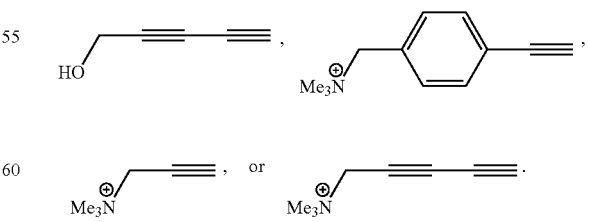

3. A composition for detecting or characterizing nucleic acid G-quadruplex formation and label-free selective sensing of potassium ion comprising a charged $d^8$ or $d^{10}$ metal complex, wherein the charged $d^8$ or $d^{10}$ metal complex electrostatically binds to a multiple-charged biomolecule to induce aggregation and self-assembly of the metal complex through metal-metal interactions, π . . . π interactions, or a combination of both interactions, and wherein the metal complex comprises at one least transition metal, at least one carbon donor ligand, and at least one corresponding coordinating ligand; and wherein the carbon donor ligand has one of the following structures:

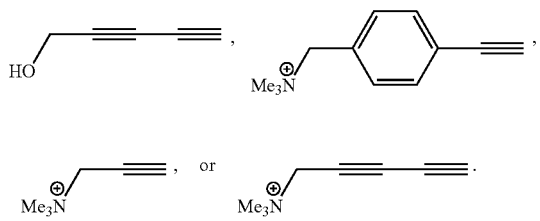

4. The composition of claim 1, wherein the self-assembly creates optical property changes to the metal complex.

5. The composition of claim 2, wherein the self-assembly creates optical property changes to the metal complex.

6. The composition of claim 3, wherein the self-assembly creates optical property changes to the metal complex.

7. The composition of claim 1, wherein the optical property change is UV/vis, emission, or CD intensity change.

8. The composition of claim 2, wherein the optical property change is UV/vis, emission, or CD intensity change.

9. The composition of claim 3, wherein the optical property change is UV/vis, emission, or CD intensity change.

10. The composition of claim 1, wherein the at least one transition metal is platinum (Pt), gold (Au), palladium (Pd), rhodium (Rh), iridium (Ir), or silver (Ag).

11. The composition of claim 2, wherein the at least one transition metal is platinum (Pt), gold (Au), palladium (Pd), rhodium (Rh), iridium (Ir), or silver (Ag).

12. The composition of claim 3, wherein the at least one transition metal is platinum (Pt), gold (Au), palladium (Pd), rhodium (Rh), iridium (Ir), or silver (Ag).

13. The composition of claim 1, wherein one or more of the corresponding coordinating ligands is a nitrogen donor ligand.

14. The composition of claim 2, wherein one or more corresponding coordinating ligands is a nitrogen donor ligand.

15. The composition of claim 3, wherein one or more corresponding coordinating ligands is a nitrogen donor ligand.

16. The composition of claim 13, wherein the nitrogen donor ligand is pyridine, bipyridine, terpyridine, polypyridine, arylpyridine, diarylpyridine, arylbipyridine, phenanthroline, diazine, triazine, phthalocyanine, imine, diimine, triimine, or porphyrin.

17. The composition of claim 14, wherein the nitrogen donor ligand is pyridine, bipyridine, terpyridine, polypyridine, arylpyridine, diarylpyridine, arylbipyridine, phenanthroline, diazine, triazine, phthalocyanine, imine, diimine, triimine, or porphyrin.

18. The composition of claim 15, wherein the nitrogen donor ligand is pyridine, bipyridine, terpyridine, polypyridine, arylpyridine, diarylpyridine, arylbipyridine, phenanthroline, diazine, triazine, phthalocyanine, imine, diimine, triimine, or porphyrin.

19. The composition of claim 1, wherein the metal complex has a planar structure or a partially planar structure, and at least one corresponding coordinating ligand is capable of π . . . π stacking interactions.

20. The composition of claim 2, wherein the metal complex has a planar structure or a partially planar structure, and at least one corresponding coordinating ligand is capable of π . . . π stacking interactions.

21. The composition of claim 3, wherein the metal complex has a planar structure or a partially planar structure, and at least one corresponding coordinating ligand is capable of π . . . π stacking interactions.

22. The composition of claim 1, wherein the at least one transition metal is platinum (Pt).

23. The composition of claim 2, wherein the at least one transition metal is platinum (Pt).

24. The composition of claim 3, wherein the at least one transition metal is platinum (Pt).

25. The composition of claim 1, wherein the at least one corresponding coordinating ligand is terpyridine.

26. The composition of claim 2, wherein the at least one corresponding coordinating ligand is terpyridine.

27. The composition of claim 3, wherein the at least one corresponding coordinating ligand is terpyridine.

28. The composition of claim 1, wherein the at least one transition metal is platinum (Pt) and at least one corresponding coordinating ligand is terpyridine.

29. The composition of claim 2, wherein the at least one transition metal is platinum (Pt) and at least one corresponding coordinating ligand is terpyridine.

30. The composition of claim 3, wherein the at least one transition metal is platinum (Pt) and at least one corresponding coordinating ligand is terpyridine.

31. The composition of claim 1, wherein the at least one carbon donor ligand has the following structure:

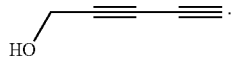

32. The composition of claim 2, wherein the at least one carbon donor ligand has the following structure:

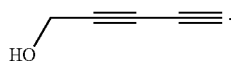

33. The composition of claim 3, wherein the at least one carbon donor ligand has the following structure:

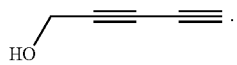

34. The composition of claim 1, wherein the at least one carbon donor ligand has the following structure:

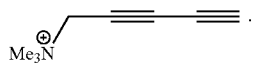

35. The composition of claim 2, wherein the at least one carbon donor ligand has the following structure:

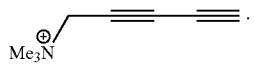

36. The composition of claim 3, wherein the at least one carbon donor ligand has the following structure:

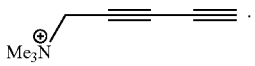

37. The composition of claim 1, wherein the at least one carbon donor ligand has the following structure:

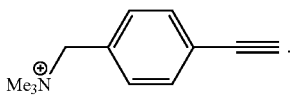

38. The composition of claim 2, wherein the at least one carbon donor ligand has the following structure:

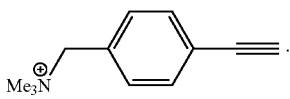

39. The composition of claim 3, wherein the at least one carbon donor ligand has the following structure:

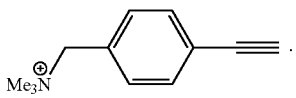

40. The composition of claim 1, wherein the at least one carbon donor ligand has the following structure:

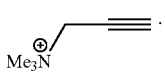

41. The composition of claim 2, wherein the at least one carbon donor ligand has the following structure:

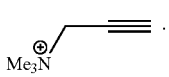

42. The composition of claim 3, wherein the at least one carbon donor ligand has the following structure:

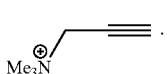

43. An assay method for detecting nucleic acid enzymatic cleavage, radical damage, or G-quadruplex formation and potassium sensing in a sample comprising:
a) combining a charged $d^8$ or $d^{10}$ metal complex as set forth in claim 1, wherein the metal complex contains at least one transition metal and at least one corresponding coordinating ligand, with the sample potentially containing the target nucleic acid under conditions effective to allow the $d^8$ or $d^{10}$ metal complex and the nucleic acid to bind to each other by electrostatic interactions, and to allow subsequent self-assembly of a charged $d^8$ or $d^{10}$ metal complex aggregate, and
b) measuring optical properties of the charged $d^8$ or $d^{10}$ metal complex aggregate.

44. A kit for use in detecting nucleic acid enzymatic cleavage, radical damage, or G-quadruplex formation and potassium sensing in a sample comprising:
a composition that contains a charged $d^8$ or $d^{10}$ metal complex as set forth in claim 1, wherein the metal complex electrostatically binds to the nucleic acid to induce aggregation and self-assembly of the $d^8$ or $d^{10}$ metal complex through metal-metal interactions and/or $\pi \ldots \pi$ interactions, and
b) instructions for use.

45. An assay method for detecting nucleic acid enzymatic cleavage, radical damage, or G-quadruplex formation and potassium sensing in a sample comprising:
a) combining a charged $d^8$ or $d^{10}$ metal complex as set forth in claim 2, wherein the metal complex contains at least one transition metal and at least one corresponding coordinating ligand, with the sample potentially containing the target nucleic acid under conditions effective to allow the $d^8$ or $d^{10}$ metal complex and the nucleic acid to bind to each other by electrostatic interactions, and to allow subsequent self-assembly of a charged $d^8$ or $d^{10}$ metal complex aggregate, and
b) measuring optical properties of the charged $d^8$ or $d^{10}$ metal complex aggregate.

46. A kit for use in detecting nucleic acid enzymatic cleavage, radical damage, or G-quadruplex formation and potassium sensing in a sample comprising:
a) a composition that contains a charged $d^8$ or $d^{10}$ metal complex as set forth in claim 2, wherein the metal complex electrostatically binds to the nucleic acid to induce aggregation and self-assembly of the $d^8$ or $d^{10}$ metal complex through metal-metal interactions and/or $\pi \ldots \pi$ interactions, and
b) instructions for use.

47. An assay method for detecting nucleic acid enzymatic cleavage, radical damage, or G-quadruplex formation and potassium sensing in a sample comprising:
a) combining a charged $d^8$ or $d^{10}$ metal complex as set forth in claim 3, wherein the metal complex contains at least one transition metal and at least one corresponding coordinating ligand, with the sample potentially containing the target nucleic acid under conditions effective to allow the $d^8$ or $d^{10}$ metal complex and the nucleic acid to bind to each other by electrostatic interactions, and to allow subsequent self-assembly of a charged $d^8$ or $d^{10}$ metal complex aggregate, and
b) measuring optical properties of the charged $d^8$ or $d^{10}$ metal complex aggregate.

48. A kit for use in detecting nucleic acid enzymatic cleavage, radical damage, or G-quadruplex formation and potassium sensing in a sample comprising:
a) a composition that contains a charged $d^8$ or $d^{10}$ metal complex as set forth in claim 3, wherein the metal complex electrostatically binds to the nucleic acid to induce aggregation and self-assembly of the $d^8$ or $d^{10}$ metal complex through metal-metal interactions and/or $\pi \ldots \pi$ interactions, and
b) instructions for use.

* * * * *